(12) United States Patent
Davison et al.

(10) Patent No.: US 10,383,962 B2
(45) Date of Patent: Aug. 20, 2019

(54) SELF-SANITIZING ELECTRICAL MACHINE

(71) Applicant: KOLLMORGEN CORPORATION, Radford, VA (US)

(72) Inventors: James Davison, Radford, VA (US); Jerry Brown, Blacksburg, VA (US); Kevin Garrison, Radford, VA (US)

(73) Assignee: KOLLMORGEN CORPORATION, Radford, VA (US)

( * ) Notice: Subject to any disclaimer, the term of this patent is extended or adjusted under 35 U.S.C. 154(b) by 0 days.

(21) Appl. No.: 15/248,312

(22) Filed: Aug. 26, 2016

(65) Prior Publication Data

US 2017/0056537 A1 Mar. 2, 2017

Related U.S. Application Data

(60) Provisional application No. 62/210,994, filed on Aug. 28, 2015.

(51) Int. Cl.
| | |
|---|---|
| *A61L 2/04* | (2006.01) |
| *B08B 7/00* | (2006.01) |
| *B08B 7/02* | (2006.01) |
| *A61L 2/025* | (2006.01) |
| *H02P 29/62* | (2016.01) |
| *A61L 2/02* | (2006.01) |
| *H02K 15/12* | (2006.01) |

(52) U.S. Cl.
CPC ......... *A61L 2/04* (2013.01); *A61L 2/02* (2013.01); *A61L 2/025* (2013.01); *B08B 7/0071* (2013.01); *B08B 7/02* (2013.01); *H02K 15/125* (2013.01); *H02P 29/62* (2016.02); *A61L 2202/14* (2013.01); *H02K 2213/03* (2013.01)

(58) Field of Classification Search
CPC ... A61L 2/04; A61L 2/02; A61L 2/025; H02K 15/125; H02K 11/33; H02P 29/62; B08B 7/02; B08B 7/0071
See application file for complete search history.

(56) References Cited

U.S. PATENT DOCUMENTS

| | | |
|---|---|---|
| 4,195,324 A | 3/1980 | Waltz |
| 2012/0181965 A1 | 7/2012 | Chamberlin et al. |
| 2015/0188480 A1 | 7/2015 | Liu et al. |

FOREIGN PATENT DOCUMENTS

DE     649565 C     8/1937

OTHER PUBLICATIONS

International Search Report, issued in corresponding international application No. PCT/US2016/048903, dated Dec. 14, 2016.
Written Opinion of the European International Searching Authority, issued in corresponding international application No. PCT/US2016/048903, dated Dec. 14, 2016.

*Primary Examiner* — Regina M Yoo
(74) *Attorney, Agent, or Firm* — Day Pitney LLP

(57) ABSTRACT

A method for sanitizing an electric motor is provided. The method includes setting operational parameters for the electric motor for destroying targeted microbes; and energizing the electric motor using the set operational parameters. Computer program products and an electric motor are disclosed.

8 Claims, 8 Drawing Sheets

SELF-SANITIZING ELECTRICAL MACHINE

CROSS REFERENCE TO RELATED APPLICATIONS

This patent application is filed under 35 U.S.C. § 111(a) and claims the benefit of priority under 35 U.S.C. § 119(e) to U.S. Provisional Patent Application Ser. No. 62/210,994, filed Aug. 28, 2015, which is incorporated by reference herein in its entirety for any purpose whatsoever.

BACKGROUND OF THE INVENTION

1. Field of the Invention

The present invention relates generally to motor technology and more particularly relates to self-sanitizing motors for use in hygienic environments.

2. Description of the Related Art

Electrical machines, such as motors, are used in many processes within food processing, pharmaceutical and packaging facilities. For example, mixers, cutters, fillers, conveyers, and packaging equipment require a variety of motors for a number of functions. In such facilities, in addition to the requirement performance in terms of reliability, energy efficiency, overall precision and control, there are additional requirements related to food safety and hygiene.

Generally, due to the complexity of the arrangements of equipment in many facilities and their size, it is an onerous task to disengage the equipment from the production line for cleaning operations, and the industry is therefore moving toward in-situ "clean-in-place" operation in which the equipment is not disengaged and cleaned in its production location. To aid such in-situ cleaning, known IP69K sealed hygienic servomotors include a stainless steel, round housing design which facilitates long life and reliable operation even in harsh food, beverage and pharmaceutical applications where the motor may be subject to frequent high-pressure wash-down cleanings. Food, beverage and pharmaceutical equipment machine builders generally use as many stainless steel components as possible. In addition, the motors and their related control and communication devices feature designs that are enclosed, encased, corrosion-resistant and capable of being washed down.

Interest in sanitary design features of motors has increased as regulations like the US Food Safety Modernization Act include specifications for facilities and machines that incorporate motors. However, in some applications simply washing down the motors may not be adequate either to fully comply with such safety regulations or, even if the letter of the regulations are satisfied, to ensure that the equipment is fully sanitized.

It would therefore be advantageous to provide electrical machines for food processing and related applications which have self-sanitizing functionality to further improve maintenance of facility hygiene.

SUMMARY OF THE INVENTION

In one embodiment, a method for sanitizing an electric motor is provided. The method includes setting operational parameters for the electric motor for destroying targeted microbes; and energizing the electric motor using the set operational parameters.

Setting the operational parameters of the electric motor may include setting a current amplitude supplied to windings of the electric motor sufficient to heat the housing of the electric motor to a temperature at which the targeted microbes will be destroyed; the temperature of the housing may be raised to at least 130 degrees Fahrenheit. Setting the operational parameters of the electric motor may include providing a current waveform of varying frequency to windings of the electric motor to cause vibration at frequencies at which the targeted microbes will be destroyed; the frequencies may be within a range from about 10 Hz to about 20 kHz.

The method may further include restoring the operational parameters to a normal setting; and returning the motor to normal operation. The method may further include monitoring at least one of temperature and vibration of the electric motor; and returning the electric motor to normal operation according to a monitoring result. The housing of the electric motor may be vibrated and heated simultaneously.

In another embodiment, a computer program product stored on machine readable media is provided, the computer program product including machine executable instructions for sanitizing an electric motor, the instructions for implementing a method. The method may include setting operational parameters for the electric motor for destroying targeted microbes; and energizing the electric motor using the set of operational parameters.

The method may further include monitoring at least one of temperature and vibration of the electric motor; and returning the electric motor to normal operation according to a monitoring result. The method may further include determining the operational parameters according to at least one of equipment data, hygienic standards and a schedule. The method may further include obtaining characterization data for the electric motor from a library of characterization data. The method may further include adjusting the operational parameters according to at least one of the characterization data for the electric motor and a function for setting operational parameters governing the sanitizing protocol.

In yet another embodiment, an electric motor configured for use in a hygienic environment is disclosed. The electric motor includes a housing including internal components configured to supply mechanical energy when supplied with an electric current; and a controller configured for controlling the electric current to control a sanitizing process for the electric motor.

The controller may include a circuit that is one of contained within the housing and mounted to the housing. The controller may include at least one of a temperature control module and a vibration control module. The controller may be in a location that is remote from housing. The controller may be configured to control at least one of the sanitizing process and initiation of the sanitizing process.

The electric motor may include one of: an induction motor; a synchronous motor; a shunt motor; a separately excited motor; a series motor; a permanent magnet motor; a compounded motor; a stepper motor; a brushless DC motor; a hysteresis motor; a reluctance motor; a universal motor; and another type of motor.

In the electric motor, the sanitizing process is configured to at least partially destroy microbial activity on the electric motor.

In yet another embodiment, a computer program product stored on machine readable media is provided, the computer program product including machine executable instructions for sanitizing an electric motor, the instructions for implementing a method. The method may include setting a target temperature for a housing of the electric motor for destroying targeted microbes; and energizing the electric motor to reach the target temperature.

The method may further include monitoring the temperature of the housing of the motor; comparing the monitored temperature of the motor with the target temperature; and adjusting a current supplied to the motor to reach the target temperature; the target temperature may be within a range of from 130 to 160 degrees Fahrenheit.

In yet another embodiment, a computer program product stored on machine readable media is provided, the computer program product including machine executable instructions for sanitizing an electric motor, the instructions for implementing a method. The method may include setting a target range of frequencies for vibrating a housing of an electric motor for destroying targeted microbes; and energizing the electric motor at the target range of frequencies.

The method may further include supplying frequency current waveform to the electric motor that includes the target range of frequencies.

In yet another embodiment, an electric motor configured for use in a hygienic environment is disclosed. The electric motor includes a housing having a surface; and a set of conductive windings arranged along and proximate to the surface of the housing, the conductive windings adapted to receive a current to heat the surface of the housing to a temperature lethal to targeted microbes.

The electric motor may be composed of stainless steel.

In yet another embodiment, an electric motor configured for use in a hygienic environment is disclosed. The electric motor includes a housing having a surface; and a set of vibrating devices adapted to cause the housing surface to vibrate at a range of frequencies lethal to targeted microbes.

In the electric motor, the range of frequencies is selected within a range from 10 Hz to 20 kHz.

DETAILED DESCRIPTION OF THE INVENTION

Figure 1:
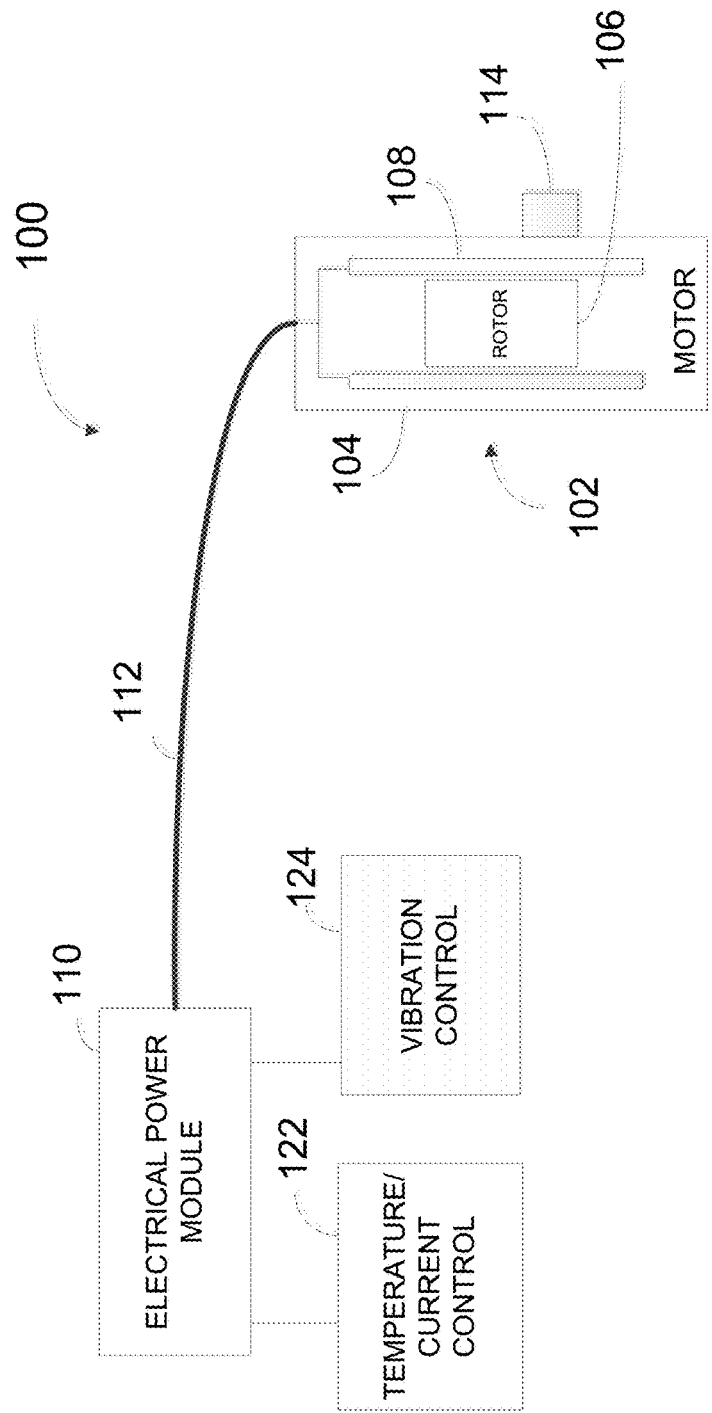
FIG. 1 is a schematic diagram of an self-sanitizing motor system according to an exemplary embodiment of the present invention.

Disclosed herein are techniques for substantially eliminating microbial activity on or in an electric motor. Advantageously, the techniques for sanitizing the electric motor take advantage of properties of the electric motor and therefore require little to no modification of the motor itself. This generally results in a substantially germ-free electric motor suited for use in a hygienic environment.

The terms "machine" and "motor" are used interchangeably within this specification and the use of one term versus the other is not intended as a limitation of scope.

The term "housing" as used herein means any structure or structures that enclose the rotor of a motor.

The term "microbe" as used herein generally refers to any microscopic organisms including but not limited to bacteria and parasites which are potentially harmful and may constitute pathogens. Generally, a quantitative limit for microbial activity may be related to and govern processes in an environment where a given electric motor may be used. Limits for microbial activity may be pathogen specific. As discussed herein, an environment where pathogens or microbial activity are controlled or regulated may be referred to as a "hygienic environment" and by other similar terms. Generally, as used herein, the term "sanitize," as well as other forms of this term, relate to reductions in microbial activity on a surface. As described herein, a sanitizing procedure is intended to reduce microbial activity to a level that meets, or substantially meets, an applicable standard, however, this is not required. For example, a sanitizing procedure may simply reduce microbial activity, with the intention that another process will be used in conjunction those processes introduced herein.

Applicable standards for hygiene and sanitizing of equipment may be promulgated by, for example, the Food and Drug Administration (FDA), the U.S. Department of Agriculture (USDA) as well as numerous state and local regulatory bodies.

In food processing and pharmaceutical facilities, among others, equipment surfaces are often fabricated from stainless steel. The stainless steel may have been machined to a precisely even finish to prevent any pooling, harboring, growth of bacteria, and prevention of formation of biofilms on the surfaces. Quite often, the equipment surfaces are to be washed-down regularly with high temperature, high-pressure water with foaming agents that produce small bubbles that disturb and kill microorganisms. While this technique has worked for many years, foodborne illness still occurs, and diligence in cleanliness is of paramount importance.

It has been discovered that by vibrating the housing of an electric motor within a range of frequencies, a high level of sanitization can be ensured. For example, targeted microbes such as *E. coli, Listeria* and *Salmonella* can be killed and/or substantially eliminated from host surfaces.

The present invention provides techniques for destroying harmful microbes using properties of production equipment in order to further discourage the growth of any bacteria which may adhere to equipment surfaces between wash-down cycles. The techniques include heating the motor housing to a temperature and for a length of time sufficient to kill the target microbes, and/or by inducing low-amplitude vibrations of the motor housing at frequencies known to also destroy the microbes. In some embodiments, both heating and vibrational modes are employed to supplement a regular cleaning procedure, either during equipment operation or pauses in operation, to further enhance equipment sanitation. In this manner, since the power regularly supplied the motor is being used for the sanitization procedures, the motor can be said to self-sanitize.

FIG. 1 is a schematic diagram of an exemplary embodiment of an self-sanitizing motor system 100. In the system 100, a motor 102 includes an outer housing 104, a rotor 106 and electrical windings 108. The motor 102 is powered remotely by an electrical power module 110 via an electrical drive cable 112. In some implementations, the electrical power module 110 is mounted on the motor 102 and the drive cable 112 may not be needed. Various sensors are collectively represented by block 114. The sensors 114 may include thermocouples or other types of sensors for measuring temperature on the housing surface and accelerometers for measuring movement of the housing. The sensors 114 may be positioned on or in the vicinity of the motor housing 104.

The motor housing 104 may be characterized as having a particular shape, size and design. Preferably, the motor 102 has a "hygienic" surface, meaning that the surface is made of an appropriate material, such as stainless steel, that may be cleaned to hygienic standards. Typically, the hygienic surface is machined to fine tolerances (e.g., on the scale of 1 micron) to remove any recesses, crevices, or other features conducive to the formation of bacterial colonies. The motor 102 may be a linear or rotary motor design and the rotor 106 and windings 108 may be of any configuration for the desired operation of the motor.

In this embodiment, the electrical power module 110 includes two control modules, a temperature control module 122 and a vibration control module 124. The temperature control module 122 allows the operator to control the phase and amplitude of current to the motor 102. The vibration control module 124 allows the operator to control the frequency of a voltage and/or current applied to the motor 102. Both the temperature control module 122 and the vibration control module 124 may be implemented electrically and/or electronically as part of the circuitry of the electrical power module 110. In some embodiments, the temperature control module 122 and the vibration control module 124 are implemented separately. Interfaces to the modules 122, 124 may use manual controls and/or software controls such as graphical user interfaces implemented by a computer system.

According to one embodiment, the temperature control module 122 modifies the current signal output to the windings 108. Depending on the implementation, the current can be provided either with or without an output torque generated by the motor 102. For motors 102 that employ permanent magnets (PM), it is possible to run current through the windings 108 without producing any torque on the rotor 106 of the motor 102. Thus for PM motors 102, current can be applied to the windings 108 to generate heat without operating the moving parts of the motor 102. The reason heat can be generated without producing torque is based upon the interaction between the current vector and the rotor magnetic field vector within the motor, which can be expressed in terms of vectors referred to as the d-axis and q-axis. If the d-axis is chosen to correspond to the magnetic field vector of the rotor, the q-axis, or quadrature axis, is at 90 degrees to this axis. The voltage vectors are out of phase with the current vectors due to the inductive nature of the windings 108. When the current is controlled in the windings 108 by the temperature module 122 so that the current vector is aligned with magnetic field d-axis, no torque is produced per ampere of motor current. However, heat is still generated because of the current flow through the windings 108.

Table 1 below includes information as to the temperature and duration (at the temperature) required to achieve a "7-log 10" (1/10 million) reduction in Salmonella bacteria for several categories of meat. A 7-log 10 reduction is a USDA performance standard promulgated for the food industry.

TABLE 1

Time to kill Salmonella (7-log10 lethality)

| Temp. (° F.) | Food product | | | | |
|---|---|---|---|---|---|
| | Roast beef | Chicken (1% fat) | Turkey (1% fat) | Chicken (1% fat) | Turkey (12% fat) |
| 130 | 121 min | | | | |
| 140 | 12 min | 25.2 min | 28.1 min | 35 min | 33.7 min |
| 150 | 72 sec | 2.7 min | 3.8 min | 4.2 min | 4.9 min |
| 158 | Instant (10 sec) | | | | |
| 160 | | 13.7 sec | 25.6 sec | 16.9 sec | 26.9 sec |
| 162 | | Instant (10 sec) | | | |
| 163 | | | | Instant (10 sec) | |
| 165 | | | Instant (10 sec) | | Instant (10 sec) |

Table 1 indicates that at temperatures starting at 130 degrees Fahrenheit, Salmonella on roast beef can be reduced. With higher temperatures, chicken and turkey, at varying levels of fat content, can also be decontaminated from Salmonella, with progressively shorter durations of heating required at higher temperatures. For example, while it takes 25.2 minutes to achieve a 7-log reduction in Salmonella on chicken with 1% fat content at 140 degrees Fahrenheit, it takes only 13.7 seconds to achieve a 7-log reduction at 160 degrees Fahrenheit.

Figure 6:
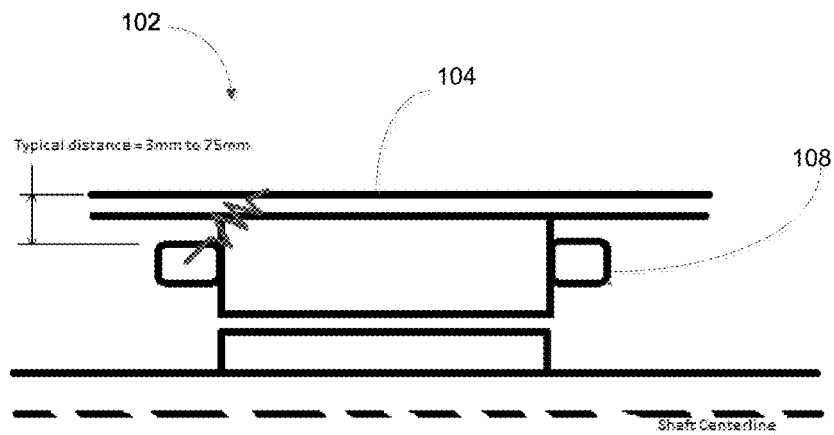
FIG. 6 is a cross-sectional view of an exemplary motor according to an embodiment of the present invention.

The current supplied to the windings 108 of the motor 102 heats and increases the temperature of the windings 108. Referring now to FIG. 6, which is a cross-sectional view of an exemplary motor, each unique motor 102 has a thermal resistance $R_{th}$ between the motor windings 108 and the surface of the motor housing 104. Units of $R_{th}$ are ° C./Watt, where ° C. is the temperature rise for a given loss in terms of Watts. A temperature rise of the motor housing can be calculated as $\Delta T [° C.] = R_{th} * P_{in}$, where $P_{in}$ is the power loss in the windings. Rth is therefore a constant that relates $P_{in}$ to $\Delta T$ for a specific motor design. In an open loop method for sanitizing a motor, an estimate of $R_{th}$ can be made based on motor size, housing material, the material of windings and the distance between the windings and the motor housing, and/or general guidelines for motor heating may be employed. The windings 108 are typically positioned in a range of from about 3 to 75 millimeters from the internal surface of the motor housing 104. The heated windings 108 exchange heat by radiation, conduction and convection with the housing 104, which rises in temperature in correlation with the heat generated in the windings. For typical motors rated between 500 W and 2 kW, it has been found that it typically takes 30 minutes to reach maximum housing surface temperature (>>160 Fahrenheit) for normal power output. Therefore, with normal operation of a motor at 500 to 2 kW it takes under 30 minutes for the housing surface to reach the temperatures required for Salmonella decontamination in accordance with the data provided in Table 1 above (130-160 degrees Fahrenheit). Therefore, using an open loop method performed without relying on temperature feedback information, the windings may be driven at 500 W or above, and a typical motor will heat up within 30 minutes to well over the 7-log 10 decontamination temperature of Salmonella.

Figure 7:
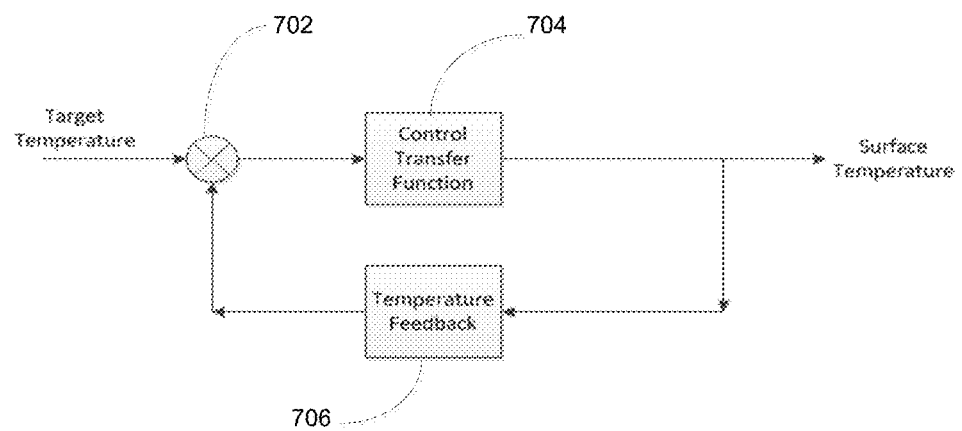
FIG. 7 is a functional control loop diagram illustrating a method of controlling the surface temperature of a motor housing according to an embodiment of the present invention.

In a closed loop method, the housing surface temperature is monitored and the temperature is controlled by adjusting current to achieve the target temperature. The closed loop method can take advantage of other sources of losses in an electrical machine, such as losses in lamination steel of permanent magnets, and these losses can also be exploited for the purpose of manipulating motor housing surface temperature. In the control loop shown in FIG. 7, in block 702, the temperature control module 122 sets a target surface housing temperature for microbe decontamination. In block 704, the temperature control module 122 then determines a control transfer function for adjusting the current provided to the motor using an algorithm that takes into account known features of the motor, including the thermal resistance ($R_{th}$) of the motor. In block 706, feedback from monitoring the surface temperature of the housing, for example using a temperature sensor 114 (FIG. 1), is communicated to the temperature control module 122. Returning to block 702, the temperature control module 122 then compares the feedback with the set temperature. Information from the comparison is passed on the control transfer function in block 704, where the current provided to the motor is adjusted if the housing surface temperature does not match the target temperature. Alternatively, if the target and surface temperatures are the same, the control transfer function makes no further adjustments. In this manner the control loop continuously monitors the housing surface temperature, and determines adjustments to be made to characteristics of the current, including its amplitude and phase, in order for the housing surface temperature to reach the target temperature.

Figure 2:
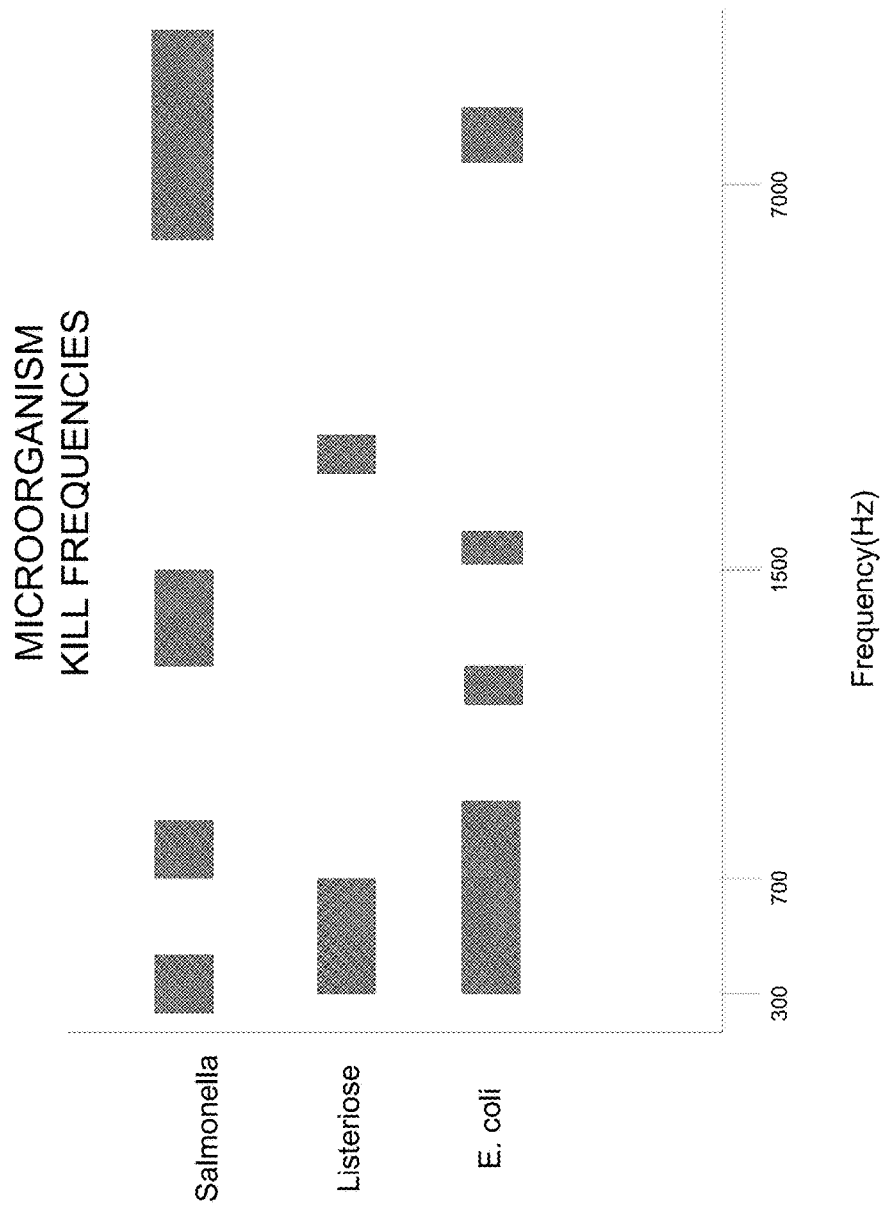
FIG. 2 is an example graph illustrating ranges of vibrational frequencies which have been found to destroy the listed microbes.

In another embodiment where control is via the vibration module 124, a non-DC current waveform is applied to the windings is varied to induce sympathetic vibrations of the housing 104. The vibrations occur in response to the excitation of the windings 108 even at low amplitudes in the current signal. The current waveform may be, for example, a sweep or chirp of an alternative current frequency range (i.e., gradually or discretely varying frequencies), or alternatively may be white noise which provides a large band of frequencies simultaneously. The range of frequencies is designed to encompass most or all of the kill frequencies of the targeted microbes to which food processing equipment is particularly susceptible. FIG. 2 shows a schematic graph illustrating ranges kill frequencies for certain selected microbes. It is noted that the values indicated are approximate and exemplary and should not be taken to be a completely accurate or exhaustive description of the kill frequencies of the included microbes.

As indicated in FIG. 2, it has been found that *Salmonella* has a group of kill frequencies in a relatively low range of between about 300 and 700 Hz and ranges of higher kill frequencies past 7 kHz. Similarly, *Listeria* and *E. Coli* have low kill frequency ranges (of about 300-1000 Hz) and higher kill frequency ranges (>7 kHz). It is noted that that bacteria may be destroyed by very low amplitudes, given the low mass of bacteria, at the specific kill frequencies. It is found that running a frequency waveform through the windings 108 of the motor 102 at the requisite frequencies itself causes enough associated mechanical vibration and further mechanisms for translating the electrical energy of the AC electrical signal into mechanical motion of the housing are not needed. In addition, during cleaning operations in which some amount of water is present on the housing, the water amplifies the effects of the vibrations and contributes to the efficacy of the vibrational mode. This is due to cavitation (bubble-formation) within the water caused by the vibration. The bubbles formed by cavitation have dimensions on the order of microbe dimensions and exert significant fluid pressure destroy which can destroy microbes with which they come into contact.

The motor housing 104 may be subjected to either the high temperature or vibrational sanitization modes or, preferably, to both modes, either simultaneously or in succession. That is, in the latter case, such as during a cleaning operation (or shortly before or afterwards) the motor may be turned on, and current supplied through the windings 108 with or without inducing torque in the motor 102, heating the motor housing 104 to a temperature required to kill target microbes and, in addition, the frequency of the current signal is varied over a range of frequencies through the windings 108 to induce low-amplitude vibrations at kill frequencies of the target microbes.

Figures 3A, 3B:
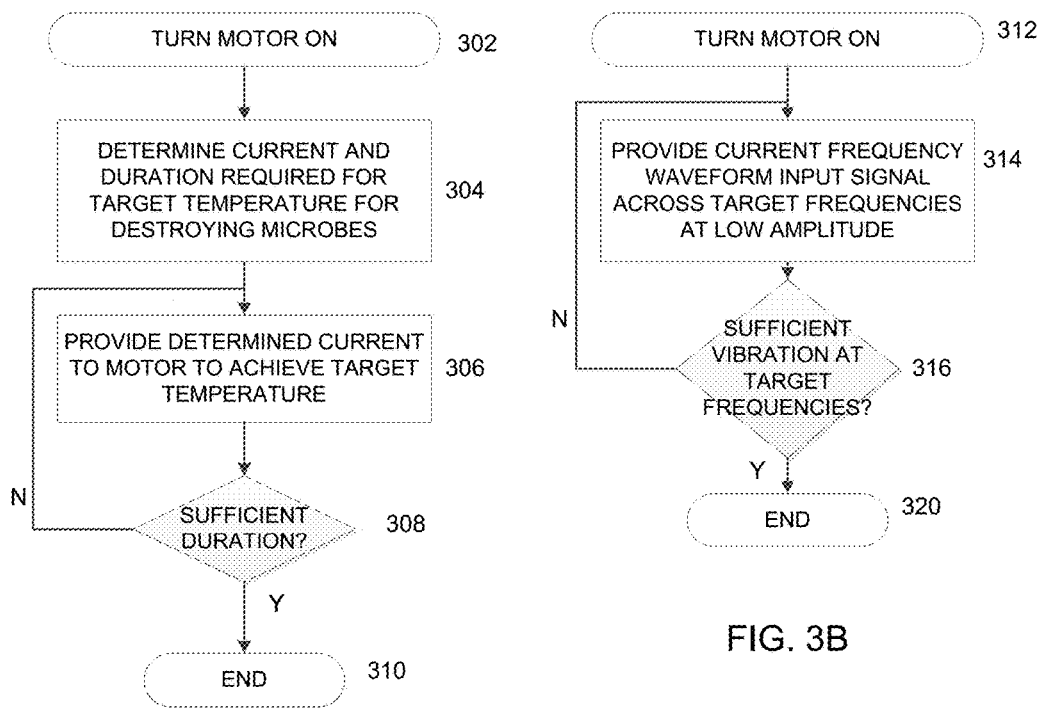
FIGS. 3A, 3B, 3C, 3D and 3E, collectively referred to herein as FIG. 3, are flow charts of methods of sanitizing a motor according to embodiments of the present invention.

FIG. 3A is a flow chart depicting an exemplary method for sanitizing a motor. In this example, the motor housing is heated to destroy targeted microbes (i.e., only high temperature mode employed). This method may be performed during or near-in-time to a wash-down cleaning of the motor, or during food production. In an initial step 302, the motor is turned on. Alternatively, if the motor is already on, it is kept on. In a second step 304, the temperature control module determines a current level and duration required for the motor housing to reach a temperature for destroying targeted microbes. The required reached temperature may be the temperature at which the most temperature-resistant microbes are destroyed. For example, if microbe species A is destroyed at temperature $T_a$, species B is destroyed at temperature $T_b$, and species C is destroyed at temperature $T_c$, with $T_c > T_b > T_a$, then the current level is set so that the motor housing reaches temperature $T_c$. In the following step 306, the electrical power module provides the determined current to the motor windings to achieve the required temperature, with or without inducing torque in the motor. In a decision step 308, it is determined whether the desired temperature has been reached and maintained for the sufficient duration. In some embodiments, this determination may involve detecting the current temperature of the housing using a temperature sensor 112, or alternatively a proxy measurement such as the amount of power output by the windings during the heating process may be used. If the duration is not sufficient, the process cycles back to step 306; otherwise the method ends (step 310).

FIG. 3B is a flow chart depicting another example of a method for sanitizing a motor. In this example, the motor housing is vibrated to destroy targeted microbes (i.e., only vibration mode employed). This method may be performed during or near-in-time to a wash-down cleaning of the motor, or during food production. In an initial step 312, the motor is turned on. Alternatively, if the motor is already on, it is kept on. In a second step 314, the vibration control module applies the frequency waveform to the motor windings to cover most or all of the kill frequencies of the target microbes (≈10 Hz to 20 kHz). As discussed above, different microbes such as *E. Coli* and *Salmonella* are vulnerable at different (multiple) frequencies, so that a range of vibrations is employed in sanitizing the motor housing. This step may be repeated one or more times. In a decision step 316, it is determined whether the motor housing has been vibrated at the target frequencies sufficiently, by ascertaining if a threshold number of sweeps of the frequency range has occurred. If the vibration of the motor housing is not sufficient, the process cycles back to step 314, otherwise the method ends (step 320).

Figure 3D:
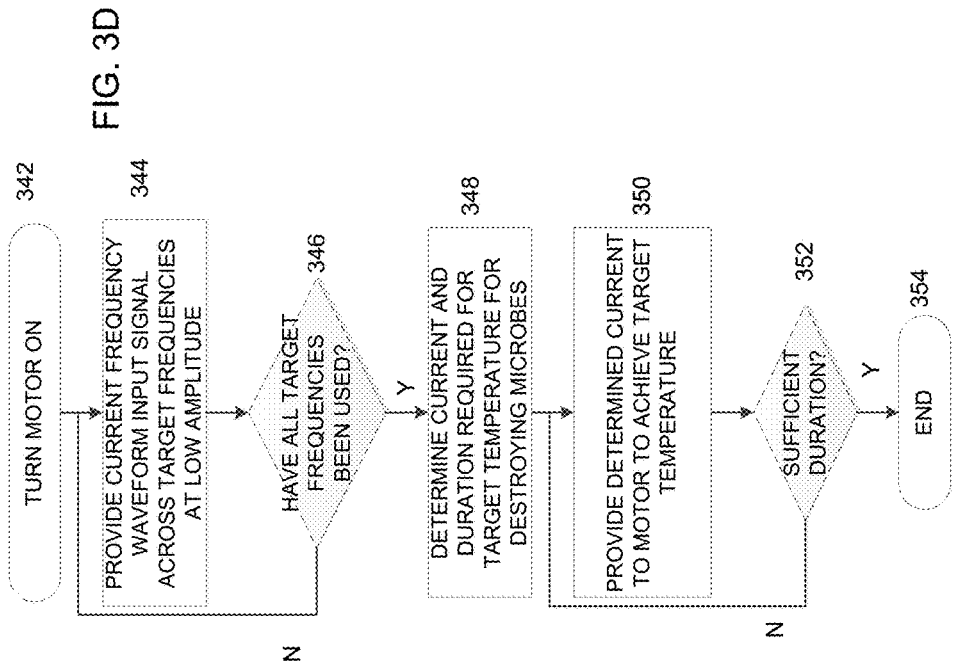
Figure 3C:
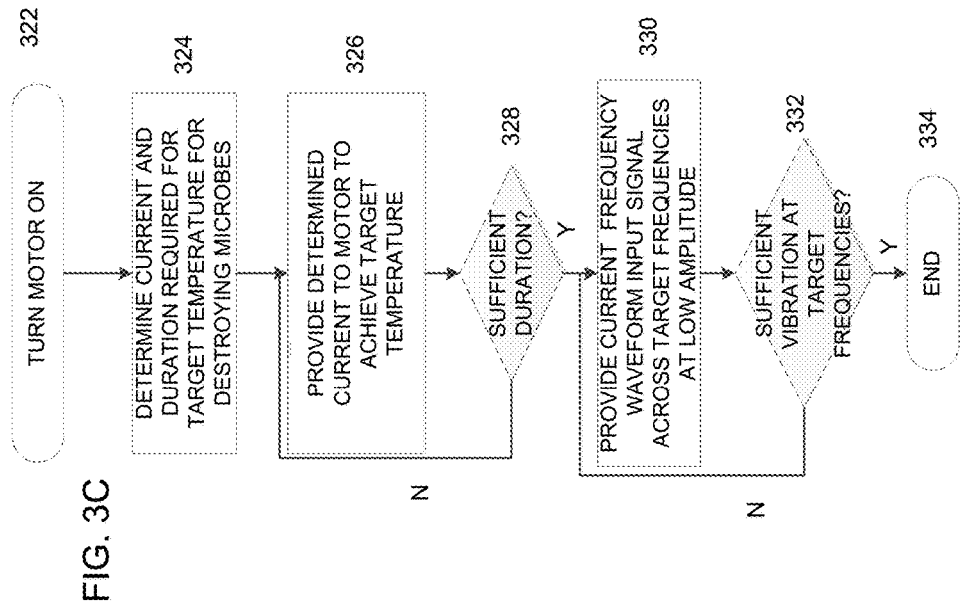

FIG. 3C is a flow chart depicting another example of a method for sanitizing a motor. In this example, the motor housing is first heated and then vibrated to destroy targeted microbes (i.e., high temperature mode and then vibration mode employed in sequence). This method may also be performed during or near-in-time to a wash-down cleaning of the motor, or during food production. In an initial step 322, the motor is turned on. Alternatively, if the motor is already on, it is kept on. In a second step 324, the temperature control module determines a current level and duration required for the motor housing to reach a temperature for destroying targeted microbes. As noted above, the required reached temperature may be the temperature at which the most temperature-resistant microbes are destroyed. In the following step 326, the electrical power module provides the determined current to the motor windings to achieve the required temperature, with or without inducing torque in the motor, depending on the type of motor used. In a decision step 328, it is determined whether the desired temperature has been reached and maintained for the sufficient duration. If the duration is not sufficient, the process cycles back to step 326; otherwise, the vibrational mode commences, in step 330, with the vibration control module applying the current frequency waveform to cover most or all of the kill frequencies of the target microbes (≈10 Hz to 20 kHz). This step may be repeated one or more times. In a decision step 332, it is determined whether the motor housing has been vibrated at the target frequencies sufficiently, by ascertaining if a threshold number of sweeps of the frequency range has occurred. If the vibration of the motor housing is not sufficient, the process cycles back to step 330, otherwise the method ends (in step 334).

FIG. 3D is a flow chart depicting yet another example of a method for sanitizing a motor. In this example, the motor housing is first vibrated and then heated to destroy targeted microbes (i.e., vibration mode and then high temperature mode employed in sequence). This method may also be performed during or near-in-time to a wash-down cleaning of the motor, or during food production. In an initial step 342, the motor is turned on. Alternatively, if the motor is already on, it is kept on. In a second step 344, the vibration control module applies the current frequency waveform to the motor windings to cover most or all of the frequencies used to kill the target microbes (≈10 Hz to 20 kHz). As discussed above, different microbes such as *E. Coli* and *Salmonella* are vulnerable at different (multiple) frequencies, so that a range of vibrations is employed in sanitizing the motor housing. This step may be repeated one or more times by. In a decision step 346, it is determined whether the motor housing has been vibrated at the target frequencies sufficiently, by ascertaining if a threshold number of sweeps of the frequency range has occurred. If the vibration of the motor housing is not sufficient, the process cycles back to step 344, otherwise the high temperature mode commences, in step 348, with the temperature control module determining a current level and duration required for the motor housing to reach a temperature for destroying targeted microbes. As noted above, the required temperature may be the temperature at which the most temperature-resistant microbes are destroyed. In the following step 350, the electrical power module provides the determined current to the motor windings to achieve the required temperature, with or without inducing torque in the motor. In a decision step 352, it is determined whether the desired temperature has been reached and maintained for the sufficient duration. If the duration is not sufficient, the process cycles back to step 350; otherwise, the method ends (in step 354).

Figure 3E:
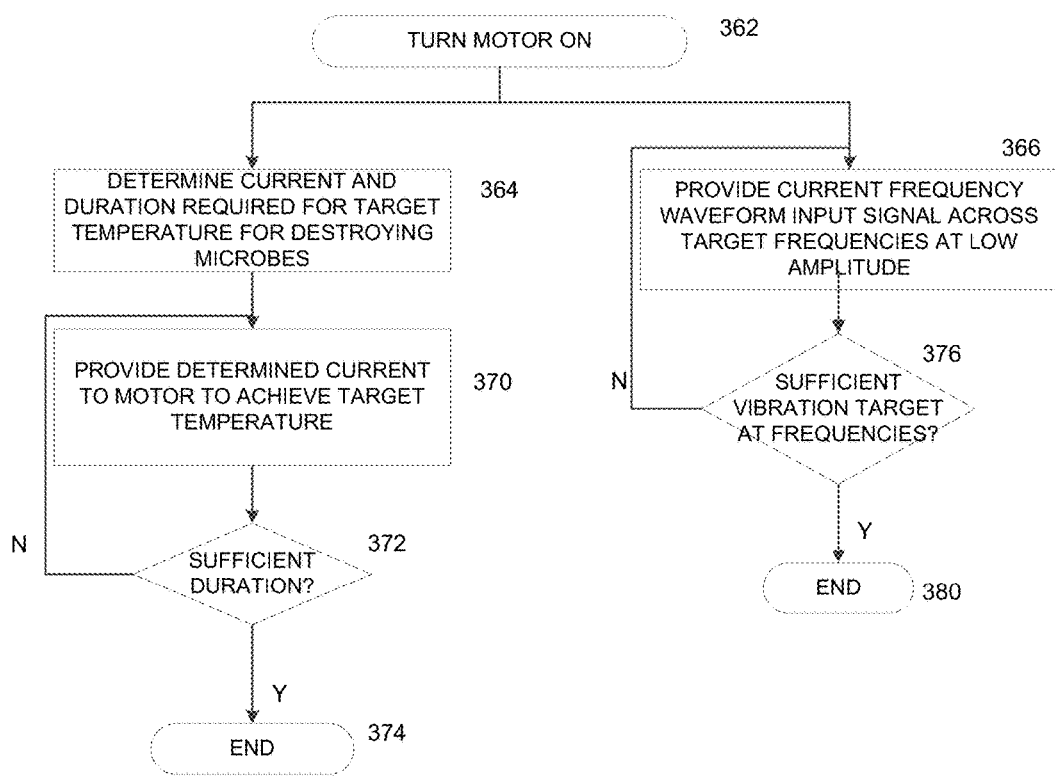

FIG. 3E is a flow chart of depicting yet another example of a method for sanitizing a motor. In this example, the motor housing is vibrated and heated simultaneously to destroy targeted microbes (i.e., vibration mode and high temperature mode employed simultaneously). This method has the advantage that it is faster to perform as both sanitization modes are performed together. This method may also be performed during or near-in-time to a wash-down cleaning of the motor, or during food production. In an initial step 362, the motor is turned on. Alternatively, if the motor is already on, it is kept on. In a second step 364, 366 the vibration control module applies the current frequency waveform to the motor windings to cover most or all of the kill frequencies of the target, and simultaneously, the temperature control module determines a current level and duration required for the motor housing to reach a temperature for destroying targeted microbes. As noted above, the required reached temperature may be the temperature at which the most temperature-resistant microbes are destroyed.

In a first branch of the method of FIG. 3E, in step 370, the electrical power module provides the determined current to the motor windings to achieve the required temperature, with or without inducing torque in the motor. In a decision step 372, it is determined whether the desired temperature has been reached and maintained for the sufficient duration. If the duration is not sufficient, the process cycles back to step 370; otherwise, the method ends (in step 374). In a second branch of the method of FIG. 3E, in a decision step 376, it is determined whether the motor housing has been vibrated at the target frequencies sufficiently, by ascertaining if a threshold number of sweeps of the frequency range has occurred. If the vibration of the motor housing is not sufficient, the process cycles back to step 366, otherwise, the method ends (in step 380).

In each of the methods of FIGS. 3A-3E discussed above, the heating and vibrational modes have been performed in closed loop, in which a decision process for determining whether a result has been achieved, i.e., a housing temperature reached or likely reached and a range of housing vibration frequencies effectuated. However, each of the heating and vibrational modes may be performed in open loop without a result-oriented decision process. Particularly when these sanitation modes are used as supplements to a regular cleaning process as an aid in to reduce risks of equipment contamination, the motor may be simply heated and/or vibrated according to a set procedure without employing sensors to detect if a result has been achieved in a closed loop.

Figure 4A:
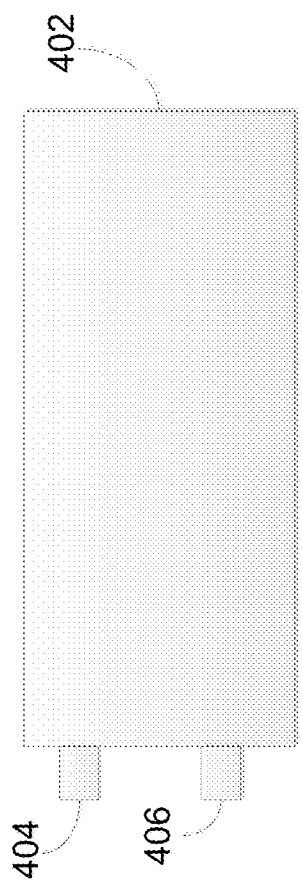
FIG. 4A is a schematic plan view of a motor having electrodes for supplying current directly to the motor housing according to an embodiment of the present invention.
Figure 4B:
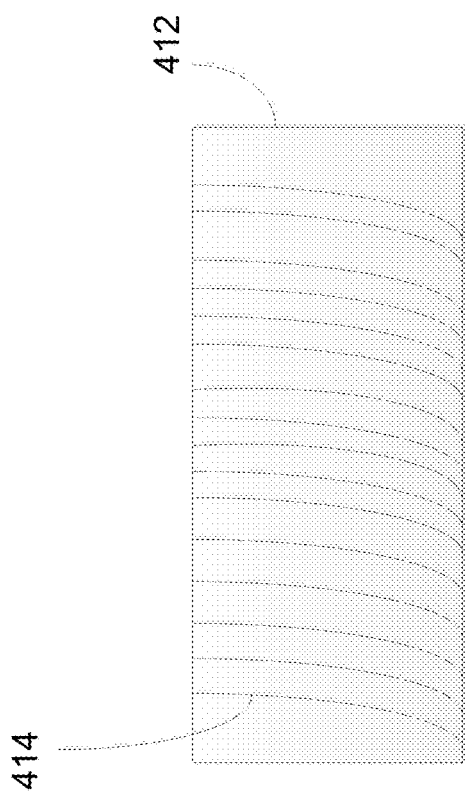
FIG. 4B is a schematic plan view of a motor having a set of conductive windings arranged proximate to the motor housing according to an embodiment of the present invention.

In some embodiments, the motor housing may be heated directly. In a first embodiment, a high frequency current is applied directed to the conductive housing, for example, by attaching electrode terminals at the ends of a power supply cable (not shown) to the housing. FIG. 4A is a schematic illustration showing a motor housing 402 with electrodes 404, 406 placed at one end for receiving a high frequency current signal. The signal will cause current to flow on the surface of the housing, which will also generate heat on the surface. This results in the heating of the housing sufficient to create an anti-microbial effect. Alternatively, an additional conductive winding may be wound around the outer surface of the machine. FIG. 4B is a schematic illustration showing a motor housing 412 and a conductive winding 414 wound around the longitudinal surface of the housing. By applying high frequency current to the winding 414, eddy currents are created induce heat in the housing to temperatures sufficient to kill harmful bacteria and viruses.

Figure 5:
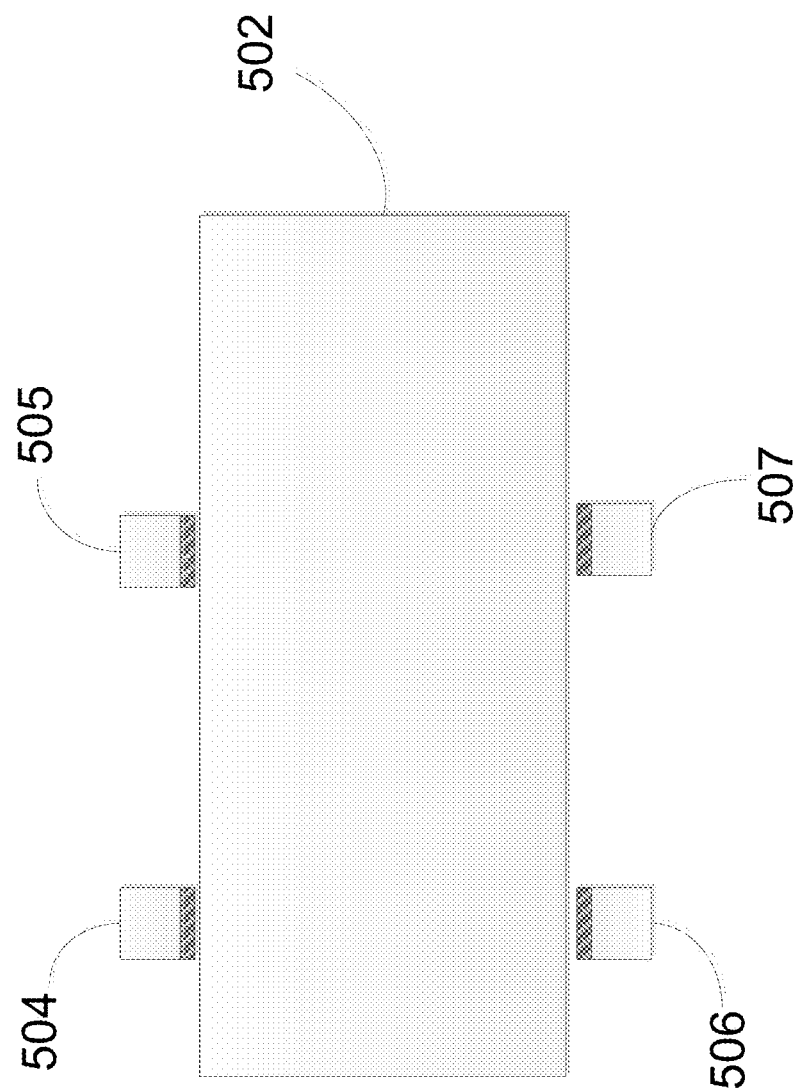
FIG. 5 is a schematic plan view of a motor having a set of vibrating devices arranged on the motor housing according to an embodiment of the present invention.

In a further embodiment, the motor housing may also be vibrated directly. In the embodiment depicted in FIG. 5, vibrating devices 504, 505, 506, 507 are disposed on the surface of a motor housing 502. Although four vibrating devices are depicted, fewer or a greater number of devices may be employed. The vibrating devices 504-507 can be activated using the vibration module according to an algorithmically set waveform and can induce vibrations of the motor housing 502 in a frequency range similar to those described above for vibrations induced by the motor winding, for example 10 Hz to 20 kHz. The vibrations encompass the kill frequency ranges of the common microbes including *E. Coli, Salmonella* and *Listeria.*

The vibrational mode may also be used as an anti-allergen measure to remove allergenic particulate matter from housing surfaces. The use of vibrations to remove allergens may be independent of wash-down cleanings and may therefore take place without any moisture on or near the motor housing surface. However, vibration alone over a range of frequencies using a frequency waveform can be sufficient to dislodge allergenic particulates and fibers of typical size ranges.

Performance of a given electric motor may be characterized. That is, for example, heat transfer characteristics of the given motor may be determined by a series of evaluations and curve fitting of the resultant data to provide a function useful for setting operational parameters governing the sanitizing protocol. Characterization may be performed with live bacteria as well. Accordingly, intervals and/or protocols required for sanitizing the given electric motor once placed into production may be well understood. Characterization data may be used to select operational parameters of power supplies to the electric motor in order to ensure adequate sanitizing takes place. In some embodiments, a library of characterization data may be stored. For example, the library of characterization data may be stored on non-transitory media, which may be remote from an installation using the electric motor.

Having thus introduced aspects of the invention, some additional features, embodiments and considerations are now set forth.

Although the foregoing embodiments are set forth with regard to food processing, it should be recognized that electric motors configured for sanitizing procedures as set forth herein may be used in other settings as deemed appropriate. For example, the drive motor may be used in industries or settings involved with food and beverage distribution; packaging and converting; pharmaceutical; material forming; medical laboratory and automation; robotics; printing; labeling; aerospace and any other environment deemed appropriate.

In this example, drive motor is a "hygienic motor." That is, the drive motor is designed to withstand the rigors of operation and periodic cleaning in an environment where standards for hygiene are imposed. As an example, the Food and Drug Administration (FDA) has set forth Current Good Manufacturing Practices (CGMP) for meat and poultry manufacturing equipment design. See "Good Manufacturing Practices (GMPs) for the $21^{st}$ Century—Food Processing, Appendix A" Aug. 9, 2004. In this guidance, the FDA has suggested standards (referred to as "preventive controls") for processing equipment. These standards include: the processing equipment should be of sanitary design; it must be cleanable down to the microbiological level; it must be made of compatible materials; it must be accessible for inspection, maintenance, cleaning, and sanitation; it must be self-draining (i.e., does not allow for product or liquid collection); it must have its hollow areas hermetically sealed; it must be free of niches; it must have sanitary operational performance; it must have its maintenance enclosures hygienically designed; it must be hygienically compatible with other plant systems; and it must have a validated cleaning and sanitizing protocol. Of course, a variety of other standards, rules or regulations may be applicable and/or promulgated by other agencies or rule making bodies.

A variety of sanitizing agents may be used to sanitize equipment such as the drive motor 102. Examples include agents containing quaternary ammonium compounds (QACs), such as peroxyacetic acid, iodine, or chlorine. A variety of other agents are known and widely used. In short, the processes set forth herein may be used in conjunction with other processes, known or to be devised, to ensure adequate or cost effective sanitizing of equipment.

The drive motor may include any type of motor deemed appropriate. For example, the drive motor be driven by alternating current (AC) or direct current (DC). For example, the drive motor may include, without limitation: an induction motor; a synchronous motor; a shunt motor; a separately excited motor; a series motor; a permanent magnet motor; a compounded motor; a stepper motor; a brushless DC motor; a hysteresis motor; a reluctance motor; a universal motor; and any one or more of a variety of other types of motors. The drive motor may include any type of material deemed appropriate. For example, stainless steel may be used. As another example, polymeric materials may be used and may include bactericides disposed therein.

Generally, at least one of the temperature control module and vibration control module may be implemented on a computer. Generally, the computer stores machine readable instructions on non-transitory machine readable media (such as in ROM, RAM, or in a mass storage unit). The machine readable instructions (which may be referred to herein as "software," as an "application," as a "client, a "process," a "plug-in" and by other similar terms) generally provide for functionality as will be discussed in detail further herein. In some embodiments, software is downloaded to memory (RAM) via a communications channel.

Some of the machine readable instructions stored on the machine readable media may include an operating environment. Software as provided herein may be developed in any language deemed suitable. Exemplary development languages include, without limitation, assembler, C (and the variants thereof), java, javascript and others. Aspects of the software may be implemented with other software. For example, user interfaces may be provided in XML, HTML and the like and implemented by a browser. Data may be stored in any type of database deemed appropriate, and manipulated with appropriate tools. For example, images, as well as the shapes and inventory of available dies may be stored in databases such as ORACLE provided by Oracle Corporation, of Redwood Shores, Calif.; SQL SERVER from Microsoft Corporation of Redmond, Wash.; and SYBASE of SAP Corporation of Dublin, Calif. Additionally, data libraries as may be generated herein (discussed below) may be managed accordingly. In short, software may be developed using any tools deemed appropriate by a user, designer, manufacturer or other similarly interested party.

Application-programming-interface (API) modules may be included with or for components such as the motor. Accordingly, at least one of the temperature control module and the vibration control module may be configured to recognize and cooperate with third party components (such as system drivers for regulating operation of the motor) as well as third party data (such as data from standards setting agencies). APIs may be provided with an original software installation, downloaded from a remote server, or otherwise made available.

The software may be configured to communicate with or receive data from the various temperatures sensors and/or vibration sensors.

Software used to implement the methods disclosed herein may host additional features. For example, the software may be configured to look up equipment data, hygienic standards and other such aspects and select routines for periodic sanitizing procedures. In some embodiments, the software may be configured with a scheduler, such that sanitizing procedures occur during off hours after the cessation of production or according to a rate schedule for reduced electric rates.

Task specific instruction sets for performing the tasks described herein may be adapted for any appropriate environment. For example, the instructions set may operate within computing environments provided by Apple Corp. of Cupertino, Calif. (iOS environments); Microsoft Corp. of Redmond Wash. (WINDOWS environments); Google Corp. of Mountain View, Calif. (Android) and other similar environments.

Computers suited for implementing at least one of the temperature control module and vibration control module may include at least one of a remote computer; a personal computer (PC); a tablet computer; a smartphone; and a specialized device. Given the highly configurable nature of computing systems, the term "computer" is to be construed to include any configuration of components and/or software as needed to provide for the intended functions as well as extensions thereof. In some embodiments, the computer includes at least one microcontroller.

The teachings herein may be used with existing equipment. For example, at least one of the temperature control module and vibration control module. In some other embodiments, the motor may be provided with on-board electronics configured to periodically execute a cycle as described herein.

It should be noted that some of the terminology set forth herein may be in agreement, or only partially an agreement with terminology set forth in the prior related provisional patent application. One skilled in the art will recognize the various uses of terms and be able to make the distinctions. However, if a conflict should exist, terminology is set forth in this disclosure shall prevail. It should be recognized that some adjustment and terminology has been provided to simplify explanation. No conflicts in terminology should be construed or inferred.

Standards for performance, materials, assembly or other such parameters are to be judged by a designer, manufacturer, user, owner, operator or other similarly interested party. No particular requirements for any standards are implied or to be inferred by the disclosure here.

As discussed herein, the electric motor may be raised to "at least a temperature of" (for example) 130 degrees Fahrenheit. This is not to be construed as an open ended range without limitation. That is, it is understood that excessive temperature may be damaging to the electric motor, and may also require extended cooling periods prior to return to normal operation. Thus, certain practical limitations should be inferred.

As discussed herein, the term "periodic" generally refers to an ongoing process. Tasks may be perceived as being performed on a periodic basis when being performed at periodic intervals that are adequate to satisfy the needs of a user and to provide a desired level of result. Accordingly, the term "periodic basis" should be construed as performance of a task at an interval or frequency that is adequate to meet a defined level of performance. The term "automatic" generally refers to initiation of a process without human interaction or initiation. The term "semi-automatic" generally refers to initiation of a process with limited human interaction or involvement.

All statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Various other components may be included and called upon for providing for aspects of the teachings herein. For example, additional materials, combinations of materials and/or omission of materials may be used to provide for added embodiments that are within the scope of the teachings herein.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements. The usage of the term "exemplary" is to be construed as meaning one of many possible embodiments. The term "exemplary" is not to be construed as being necessarily indicative of a superior or superlative embodiment, although, in some instances this may be the case.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for sanitizing an electric motor, the method comprising:
    setting operational parameters for the electric motor for destroying targeted microbes, the operational parameters including a target temperature and a determined current level and duration of time required to reach the target temperature;
    energizing the electric motor to the target temperature using the set operational parameters;
    monitoring a temperature of the electric motor and the duration of time of heating;
    adjusting a current supplied to the electric motor to reach the target temperature; and
    comparing the monitored temperature of the electric motor with the target temperature.

2. The method of claim 1, wherein setting the operational parameters of the electric motor comprises setting a current amplitude supplied to windings of the electric motor sufficient to heat a housing of the electric motor to the target temperature at which the targeted microbes will be destroyed.

3. The method of claim 2, wherein the temperature of the housing is raised to at least 130 degrees Fahrenheit.

4. The method of claim 1, wherein setting the operational parameters of the electric motor comprises providing a current waveform of varying frequency to windings of the electric motor to cause vibration at frequencies at which the targeted microbes will be destroyed.

5. The method of claim 4, wherein the frequencies are within a range from about 10 Hz to about 20 kHz.

6. The method of claim 1, further comprising:
   restoring the operational parameters to a normal setting; and
   returning the electric motor to normal operation.

7. The method as in claim 1, further comprising:
   monitoring at least one of temperature and vibration of the electric motor; and
   returning the electric motor to normal operation according to a monitoring result.

8. The method of claim 1, wherein a housing of the electric motor is vibrated and heated simultaneously.

\* \* \* \* \*